US011448536B2

(12) United States Patent
Ramakrishnan et al.

(10) Patent No.: US 11,448,536 B2
(45) Date of Patent: Sep. 20, 2022

(54) MEASURING COMPONENT CONCENTRATIONS OF NONHOMOGENEOUS IMMISCIBLE MIXTURES IN MULTIPHASE FLOWS USING NEAR-INFRARED (NIR) FILTER PHOTOMETRY

(71) Applicant: Weatherford Technology Holdings, LLC, Houston, TX (US)

(72) Inventors: Vijay Ramakrishnan, Kingwood, TX (US); John Lievois, Houston, TX (US)

(73) Assignee: WEATHERFORD TECHNOLOGY HOLDINGS, LLC, Houston, TX (US)

( * ) Notice: Subject to any disclaimer, the term of this patent is extended or adjusted under 35 U.S.C. 154(b) by 518 days.

(21) Appl. No.: 16/654,672

(22) Filed: Oct. 16, 2019

(65) Prior Publication Data

US 2021/0116276 A1 Apr. 22, 2021

(51) Int. Cl.
*G01F 1/66* (2022.01)
*G01F 1/661* (2022.01)
(Continued)

(52) U.S. Cl.
CPC ............... *G01F 1/661* (2013.01); *G01J 1/04* (2013.01); *G01N 21/3504* (2013.01); *G01J 1/0271* (2013.01); *G01N 33/2847* (2013.01)

(58) Field of Classification Search
CPC ........... G01F 1/661; G01J 1/04; G01J 1/0271; G01N 21/3504; G01N 33/2847;
(Continued)

(56) References Cited

U.S. PATENT DOCUMENTS 3,677,652 A * 7/1972 Little ................. G01N 21/05
250/353
6,076,049 A 6/2000 Lievois et al.
(Continued)

FOREIGN PATENT DOCUMENTS

GB 2267963 A * 12/1993 ........... G08B 17/103

OTHER PUBLICATIONS

E.V. Zaitcev, et al., The Infrared Method of Determining The Water-Cut of a Nonhomogeneous Water-Gaz-Oil Stream, Society of Petroleum Engineers, 2016, 8 pages, SPE-182105-MS, Society of Petroleum Engineers, Moscow, Russia.
(Continued)

*Primary Examiner* — Marcus H Taningco
(74) *Attorney, Agent, or Firm* — Blank Rome LLP (57) ABSTRACT

Near-Infrared (NIR) filter photometry is used to calculate component concentrations in multiphase flows. The disclosed methodology adapts the Beer-Lambert law for nonhomogeneous immiscible mixtures (such as oil and water) by modeling the fluid layer as a nonhomogeneous distribution of its components and deriving a mathematical relationship between measured absorbances, component path lengths, and non-homogeneity factors. The methodology is integrated into a multi-channel filter photometer to measure phase concentrations in oil-and-gas pipelines. The system is proven more accurate than current state of the art based on data from simulations, multiphase flow laboratories and field trials.

20 Claims, 5 Drawing Sheets

(51) Int. Cl.
    *G01J 1/04*         (2006.01)
    *G01N 21/3504*    (2014.01)
    *G01J 1/02*         (2006.01)
    *G01N 33/28*      (2006.01)

(58) Field of Classification Search
    CPC ........... G01N 21/8507; G01N 33/2823; G01N 2021/3148; G01N 2201/0833; G01N 21/359
    See application file for complete search history.

(56) References Cited

U.S. PATENT DOCUMENTS

| | | | |
|---|---|---|---|
| 6,292,756 | B1 | 9/2001 | Lievois et al. |
| 10,054,537 | B2 | 8/2018 | Arifin et al. |
| 2008/0135761 | A1* | 6/2008 | Lievois .............. G01N 21/3554 250/339.09 |
| 2010/0138169 | A1 | 6/2010 | Johansen et al. |
| 2011/0114832 | A1 | 5/2011 | Lievois et al. |
| 2012/0046870 | A1 | 2/2012 | Lievois et al. |
| 2012/0080587 | A1 | 4/2012 | Lievois et al. |
| 2012/0251335 | A1 | 10/2012 | Hurst et al. |
| 2012/0318502 | A1 | 12/2012 | Lievois et al. |
| 2013/0146757 | A1 | 6/2013 | Lievois et al. |

OTHER PUBLICATIONS

Int'l Search Report and Written Opinion in PCT Appl. PCT/US2020/050369, dated Dec. 7, 2020.
Quayle (BP), et al., "Qualification of Weatherford's Red Eye near infrared Water Cut Probe," Weatherford Int'l, 14 pages.
Unalmis, et al., "Subsea Multiphase Flow Measurement—A New Approach," Weatherford Int'l, 30th International North Sea Flow Measurement Workshop, Oct. 2012, 16 pages.
"Red Eye® Multiphase Water-Cut Meter", Weatherford Int'l, 2008, 8 pages.
"Red Eye® 2G Hot-Tap Water-Cut Meters, Installed Offshore in Total Crude Export Line Provide Real-Time Flow Measurements for Proactive Production Management," Weatherford Int'l, 2016, 1 page.
"Red Eye® 2G Installation, Configuration, and Operation Manual," Weatherford Int'l, Aug. 2008 (Revision G), 112 pages.
"Red Eye® Series of Water-Cut Meters, Consistently accurate water-cut measurements in tough oilfield conditions," Weatherford Int'l, 2015, 8 pages.
"Red Eye® Subsea Water-Cut Meter for Multiphase Applications," Weatherford Int'l, 2014, 8 pages.
"Red Eye® Water-Cut Meter Eliminates Hand-Sampling for Improved, Automated Well Testing," Weatherford Int'l, 2010, 1 page.

* cited by examiner

MEASURING COMPONENT CONCENTRATIONS OF NONHOMOGENEOUS IMMISCIBLE MIXTURES IN MULTIPHASE FLOWS USING NEAR-INFRARED (NIR) FILTER PHOTOMETRY

BACKGROUND OF THE DISCLOSURE

Water-cut meters, such as narrow-band near-infrared (NIR) filter photometers, are used in petroleum and petrochemical industries to measure water concentration in process fluids. "Water-cut" (WC) or "Water Liquid Ratio" (WLR) refers to the volumetric ratio of water volume to total liquid volume. Examples of such devices are disclosed in U.S. Pat. Nos. 6,076,049 and 6,292,756, which are incorporated herein by reference. Additional teachings can be found in U.S. Pub. Nos. 2010/0138169, 2011/0114832, 2012/0046870, and 2013/0146757, which are incorporated herein by reference.

Overall, NIR water-cut meters use the Beer-Lambert law, either directly or with simple adaptations, to calculate component concentrations of oil and water based on measured absorbances at a few predetermined wavelengths. The components typically have large differences in the absorption of radiation at these wavelengths, thus allowing the water-cut meter to quantify their proportions.

Figure 1A:
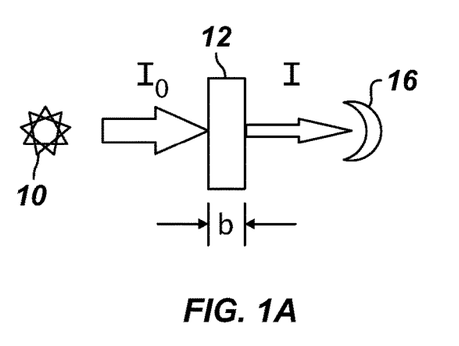
FIGS. 1A-1B illustrate principles of operation for a NIR water-cut meter according to the prior art.

FIG. 1A diagrams the principles of the Beer-Lambert law (for a solution or a mixture that is miscible and homogeneous), which is characterized by:

$$\frac{I}{I_0} = e^{-abc}$$

where: $I_0$=incident light intensity,
I=transmitted light intensity,
a=absorption coefficient,
b=optical path length, and
c=concentration.
Beer-Lambert law is also written as:

$$-\ln\left(\frac{I}{I_0}\right) = A = abc$$

where: A=absorbance.

As schematically shown, a light source 10 emits incident light $I_0$ through a path length b of a fluid layer 12, and a detector 16 measures the transmitted light I. By measuring A (or $I_0$ and I), and by knowing a and b, the concentration c of the component in the fluid layer 12 can be calculated.

Figure 1B:
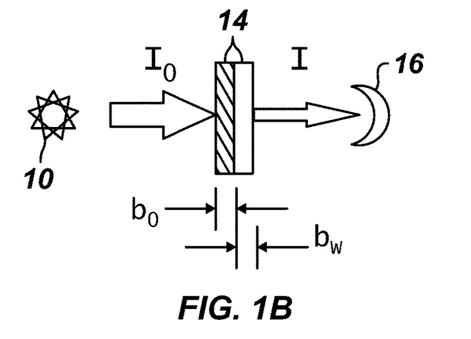

FIG. 1B diagrams the principles of the Beer-Lambert law adapted for immiscible components homogeneously-distributed (modeled as stratified layers), which is characterized by:

$$A = a_w b_w + a_o b_o + Sc$$

where: A=absorbance,
$a_w$=wavelength-specific water absorption,
$a_o$=wavelength-specific oil absorption,
$b_w$=water (optical) path length,
$b_o$=oil (optical) path length, and
Sc=wavelength-independent scatter.

As schematically shown, a light source 10 emits incident light $I_0$ through the path lengths $b_o$ and $b_w$ of fluid layers 14 (such as oil and water), and a detector 16 measures the transmitted light I. By measuring A (in at least three wavelengths), and by knowing $a_w$ and $a_o$, the path lengths $b_w$ and $b_o$ (and the Scatter Sc) in the fluid layers 14 can be calculated; these path lengths can then be used to calculate water-cut, $WC=b_w/(b_w+b_o)$.

The Beer-Lambert law, in its basic form (as described with reference to FIG. 1A), requires complete miscibility of the components and, by extension, spatial homogeneity of the mixture. Some adaptations of the Beer-Lambert law (as described with reference to FIG. 1B) relax the miscibility requirement but still require spatial homogeneity of the mixture (in at least two, if not all three, spatial dimensions). For this reason, a typical NIR filter photometer may function poorly when analyzing mixtures that are nonhomogeneous and immiscible, such as found in multiphase flows.

Multiphase (and wet-gas) flows are common in pipelines in the oil-and-gas industry, and they typically involve gas, water, and oil (or condensate) produced from the reservoir. Oil and water are immiscible; and the flowing mixture is typically nonhomogeneous, particularly in the presence of gas. Some multiphase flow situations may additionally involve methanol/glycol (injected into the pipeline for hydrate inhibition). Measuring component concentrations (such as water-in-oil and water-in-glycol ratios) in these flow situations is valuable (for production-monitoring, flow-assurance and reservoir management), but difficult. A NIR filter photometer is one of the very few devices that can reliably perform these measurements.

The subject matter of the present disclosure is directed to overcoming, or at least reducing the effects of, one or more of the problems set forth above.

SUMMARY OF THE DISCLOSURE

A method disclosed herein is directed to measuring a mixture in a multiphase flow. The mixture is nonhomogeneous and has at least two immiscible components. Spectral energy of at least four wavelengths is emitted at initial intensity for transmission through the mixture; and transmitted spectral energy of the at least four wavelengths is detected at resultant intensity after transmission through the mixture. An absorbance measurement of the mixture is determined from the initial and resultant intensities at each of the at least four wavelengths.

Each of the absorbance measurements is characterized as a first function of at least two pathlengths of the at least two immiscible components, a scatter parameter, and a non-homogeneity parameter. The scatter parameter represents attenuation of the transmitted spectral energy independent of the wavelengths. The non-homogeneity parameter represents non-homogeneity of the mixture using a plurality of cells of the transmitted spectral energy through the mixture. The at least two pathlengths of the at least two immiscible components are different for each cell.

In the end, first concentrations of the at least two immiscible components in the mixture are determined from the characterization of the absorbance measurements as the first function. For example, the method can comprise solving for the at least two pathlengths of the at least two immiscible components from the characterization of the absorbance measurements. Then, the first concentrations of the at least two immiscible components in the mixture can be determined from the solution of the at least two pathlengths.

In emitting the spectral energy, near-infrared light can be emitted. Detection of the transmitted spectral energy can involve detecting at particular wavelengths of 1110-nm, 1450-nm, 1632-nm, 1730-nm, and 1950-nm.

In the method, the initial intensity of the emitted spectral energy can be detected with a reference measurement. In this way, the detected initial intensity from the reference measurement can be used in the determination of the absorbance measurements. This reference measurement can be obtained using one or more reference detectors measuring a current intensity of the emitted spectral energy.

Alternatively in the method, the emission of the spectral energy at the initial intensity can be initially calibrated by obtaining a baseline measurement of the initial intensity transmitted without the mixture. The baseline measurement can be stored so it can be use for the initial intensity in the determination of the absorbance measurements.

In the method, the detection of the transmitted spectral energy can also be initially calibrated by detecting the transmitted spectral energy at a first of the resultant intensity after transmission through only a first of the at least two immiscible components of the mixture and detecting the transmitted spectral energy at a second of the resultant intensity after transmission through only a second of the at least two immiscible components of the mixture. In this way, absorption coefficients can be derived for the first and second immiscible components of the mixture by analyzing the first and second resultant intensities.

Overall, characterizing each of the absorbance measurements as the first function can comprise using the Beer-Lambert law at each of the cells. The non-homogeneity parameter representing the non-homogeneity of the components in the mixture can comprise a value analogous to a slope for a division in the cells between a first of the at least two pathlengths for water, as one of the at least two immiscible components, and a second of the at least two pathlengths for oil, as another of the at least two immiscible components. Accordingly, to determine the first concentrations, unknown variables of the water path length, the oil path length, the scatter parameter, and the non-homogeneity parameter can be solved for from the first functions for the absorbance measurements at four of the at least four wavelengths.

In general, detecting the transmitted spectral energy of the wavelengths at the resultant intensity after transmission through the mixture can comprise transmitting the transmitted spectral energy in a plurality of sets of randomized bundles of optical fibers respectively to a plurality of photodiodes.

In a further aspect of the method, each of at least three of the absorbance measurements can also be characterized as a second function based on the mixture having homogeneous layers of the at least two immiscible components. In this way, second concentrations of the at least two immiscible components in the mixture can be determined from the characterization of the absorbance measurements as the second function. This gives first and second concentration values, which can be selected in the method, so a final output for final concentrations of the components can be determined based on the selection. For example, selecting the first and second concentrations can comprise weighting the first and second concentrations based on a ratio of water, as one of the at least two immiscible components, relative to total liquid volume in the mixture. The weighting can favor the first concentrations for a higher ratio of the water relative to the total liquid volume in the mixture, and can favor the second concentrations for a lower ratio of the water relative to the total liquid volume in the mixture.

Finally, in the method, the multiphase flow can be measured through piping, for example, using a flowmeter. A liquid volume of the measured flow can be calculated, and a ratio of water, as one of the at least two immiscible components, relative to the liquid volume can be calculated by multiplying the calculated liquid volume by the first concentration determined for water.

A method disclosed herein is directed to measuring a mixture in a multiphase flow. The mixture is nonhomogeneous and has at least two immiscible components. Spectral energy of at least four wavelengths is emitted at initial intensity for transmission through the mixture, and transmitted spectral energy of the at least four wavelengths is detected at resultant intensity after transmission through the mixture. An absorbance measurement of the mixture at each of the at least four wavelengths is determined from the initial and resultant intensities.

The method comprises solving for at least two pathlengths of the at least two immiscible components from the absorbance measurements. Each of the absorbance measurements is a function of the at least two pathlengths through the at least two immiscible components, a scatter parameter, and a non-homogeneity parameter. The scatter parameter represents attenuation of the transmitted spectral energy independent of the wavelengths. The non-homogeneity parameter represents the non-homogeneity of the mixture by using a plurality of cells of the transmitted spectral energy through the mixture in which the at least two pathlengths of the at least two immiscible components are different for each cell. Concentrations of the at least two immiscible components in the mixture are determined from the solution of the at least two pathlengths.

According to the presented disclosure, a non-transitory program storage device comprises instructions stored thereon to cause an apparatus to perform steps of the methods disclosed above. For example, a non-transitory program storage device comprises instructions stored thereon to cause an apparatus for analyzing a nonhomogeneous mixture of immiscible components in a multiphase flow to: emit spectral energy of at least four wavelengths at initial intensity for transmission through the mixture; detect transmitted spectral energy of the at least four wavelengths at resultant intensity after transmission through the mixture; determine, from the initial and resultant intensities, an absorbance measurement of the mixture at each of the at least four wavelengths; characterize each of the absorbance measurements as a first function of at least two pathlengths of the at least two immiscible components, a scatter parameter, and a non-homogeneity parameter, the scatter parameter representing attenuation of the transmitted spectral energy independent of the wavelengths, the non-homogeneity parameter representing the non-homogeneity of the mixture using a plurality of cells of the transmitted spectral energy through the mixture in which the at least two pathlengths of the at least two immiscible components are different for each cell; and determine, from the characterization of the absorbance measurements as the first function, first concentrations of the at least two immiscible components in the mixture.

An apparatus disclosed herein is directed to analyzing a nonhomogeneous mixture of immiscible components in a multiphase flow. The apparatus comprises a probe, one or more sources, one or more detectors, and a processing unit. The probe has first and second windows, which oppose one another by a gap for the fluid in the flow. The one or more sources emit spectral energy of at least four wavelengths at initial intensity from the first window for transmission through the mixture in the gap to the second window. The one or more detectors in optical communication with the second window detect transmitted spectral energy of the at least four wavelengths at resultant intensity after transmission through the fluid.

The processing unit is configured to perform steps of the methods disclosed above. For example, the processing unit in communication with the one or more detectors is configured to: determine, from the initial and resultant intensities, an absorbance measurement of the mixture at each of the at least four wavelengths; characterize each of the absorbance measurements as a first function of at least two pathlengths of the at least two immiscible components, a scatter parameter, and a non-homogeneity parameter, the scatter parameter representing attenuation of the transmitted spectral energy independent of the wavelengths, the non-homogeneity parameter representing the non-homogeneity of the mixture using a plurality of cells of the transmitted spectral energy through the mixture in which the at least two pathlengths of the at least two immiscible components are different for each cell; and determine, from the characterization of the absorbance measurements as the first function, first concentrations of the at least two immiscible components in the mixture.

The foregoing summary is not intended to summarize each potential embodiment or every aspect of the present disclosure.

DETAILED DESCRIPTION OF THE DISCLOSURE

Figure 2:
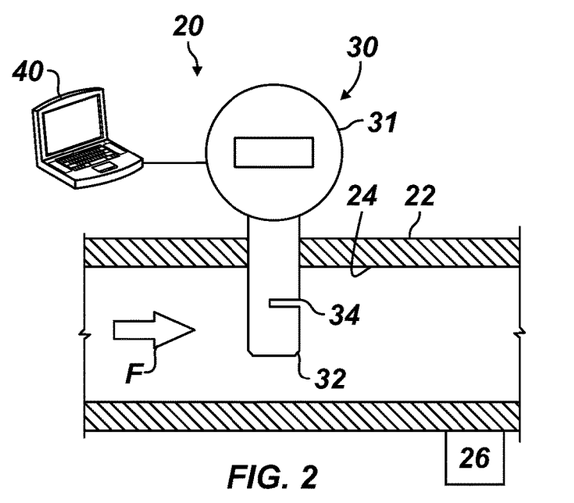
FIG. 2 illustrates a system according to the present disclosure to measure component concentrations of nonhomogeneous immiscible mixtures in a multiphase flow using NIR photometry.

FIG. 2 illustrates a system 20 according to the present disclosure having a near-infrared (NIR) filter photometer 30 using NIR photometry to calculate component concentrations of nonhomogeneous immiscible mixtures in a multiphase flow F. The system 20 can further include one or more flowmeters 26, which is only schematically shown and can include a multi-phase flowmeter, a Coriolis flowmeter, a gas flowmeter, or other type of flowmeter depending on the implementation.

As shown, the photometer 30 includes a probe 32 disposed in the multiphase flow F, such as passing through the bore 24 of a piping arrangement 22 found in oil and gas installations, well sites, etc. For example, the probe 32 can be sealably mounted in the piping arrangement 22 using known techniques. A sensor window or slot 34 on the probe 32 allows for entry of the multiphase flow F between opposing windows (35a-b; FIG. 4B) inside the probe 32. As will be appreciated, placement and orientation of the slot 34 relative to the flow F and the piping arrangement 22 can be considered based on the implementation, direction of the flow, speed of the flow, etc. For example, in flow streams having a high Gas Volume Fraction (GVF), the slot 34 may be positioned closer to the pipe wall.

As shown, the probe 32 may be connected to a local electronics package 31, which in turn may be connected to remote processing equipment 40. Other configurations of electronics and processing capabilities can be used depending on the implementation.

In one example configuration, the disclosed photometer 30 can be used in conjunction with a gas flow meter 26 and a chemical injection unit (not shown) at a gas well production header to control the feed of the inhibitor chemicals into the flow stream. The flow stream from the gas well is passed through the gas flowmeter 26 and photometer 30, and each component (gas, water, and oil) rate is measured.

In another example configuration, the disclosed photometer 30 can measure the proportion of water, oil, and hydrate-inhibitor chemicals (such as methanol, glycol) in the liquid stream at a gas well production header. This measurement is then used in real time to optimize injection of corrosion-inhibiting and hydrate-inhibiting chemicals into the pipeline 22 from the chemical injection unit (not shown).

In another example configuration, the photometer 30 can measure proportion of water in a liquid hydrocarbon stream F, such as on a pipeline 22 or at loading terminals where transfer of liquid hydrocarbons (such as crude oil or fuels) takes place. The disclosed system 20 can be used for these and other configurations.

Briefly, the system 20 uses the filter photometer 30 to measure absorbances at a number of discrete wavelengths. The wavelengths are chosen based on distinct absorptive characteristics of the components (e.g., water, oil, glycol) in the multiphase flow F. For the present purposes, near-infrared wavelengths are suitable. An NIR emitter in the probe 32 on one side of the windowed slot 34 exposes the mixture of the fluid F to broadband NIR radiation, and one or more detectors in the probe 32 on the other side of the windowed slot 34 detect the transmitted spectral energy at aforementioned discrete wavelengths. In turn, the system 20 calculates component concentrations of the mixture in the sensor slot 34 using the relationship between pure (component) absorbances and measured (mixture) absorbances.

Figure 3A:
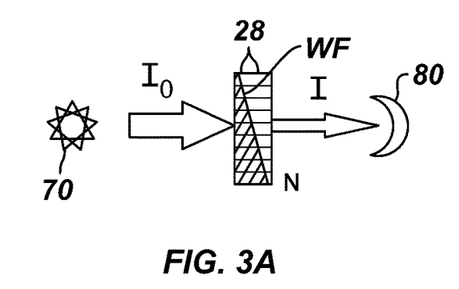
FIGS. 3A-3C illustrates graphical representations related to the principle of operation for the disclosed system.
Figure 3B:
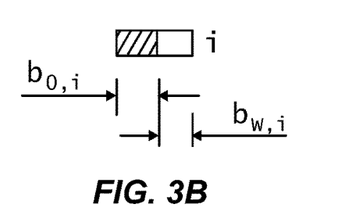

To do this, the disclosed system 20 uses a principle of operation schematically shown in FIGS. 3A-3B. In FIG. 3A, a light source 70 emits incident spectral intensity (e.g., NIR light) $I_0$ through fluid layers 28 in the sensor slot (34), and one or more detectors 80 measure the transmitted spectral intensity I. Preferably, multiple detectors 80 are provided-one for each wavelength of interest. Other arrangements may use less detectors 80 provided acceptable optical routing, filtering, multiplexing, chopper wheels, and other known techniques are used.

Figure 3C:
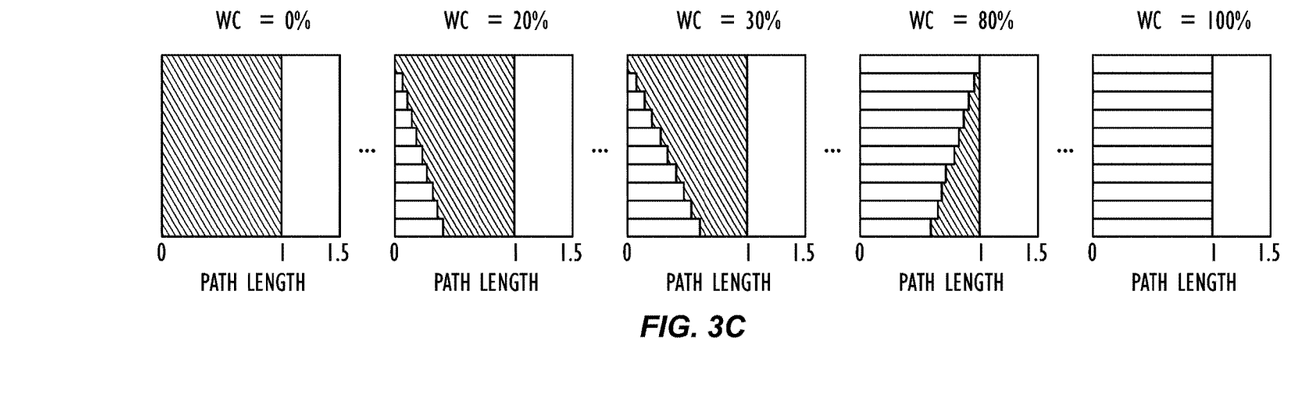

Because the fluid layers 28 may be of a multiphase flow with a mixture that is nonhomogeneous and immiscible, the analysis is divided into a number N of cells or columns, as schematically shown, each with its own path lengths $b_{o,i}$, $b_{w,i}$, for two components (e.g., oil and water) as shown in FIG. 3B for an i-th cell. FIG. 3C shows a nonhomogeneous distribution at a number of representative water-cut percentages, 0%, 20%, 30%, 80%, and 100%.

In general, the cells represent a mathematical construct that accounts for the fact that each photon of spectral energy transmitted through the mixture and detected by the detectors does not necessarily pass through the same path lengths (of the immiscible components) as the other photons when the mixture is non-homogeneous. In fact, the spectral energy from the source (70) of the photometer (30) is transmitted across an area (of the windows 35*a-b*) and through a volume of the mixture (in the gap 34) and is detected in a randomized fashion (by the bundles 39) with the plurality of detectors (80); so the spectral energy encounters the non-homogeneous mixture with its immiscible components in a distributed fashion.

If oil and water were homogeneously distributed in the sensor slot, the effective $b_o$ would be the same in all cells/columns and the effective $b_w$ would be the same in all cells/columns; and hence the fluid media would effectively be the same as the arrangement shown in FIG. 1B (i.e., with a uniform distribution of oil and water). However, the mixture is nonhomogeneous and immiscible. For this reason, as shown in FIG. 3A, the division between the components is represented by a sloped line WF. In general, the sloped line WF is a parameter that represents the non-homogeneity of the mixture. Solutions of the absorbance equations for a nonhomogeneous mixture, as discussed later, can then calculate the concentration of the two components. The cells in FIG. 3A are shown with a triangular distribution to illustrate the concept by contrasting it with FIG. 1B, but any distribution (such as Gaussian) is equally valid for the disclosed methodology.

According to the present disclosure, the system 20 calculates component concentrations in nonhomogeneous mixtures involving two immiscible fluid components (e.g., oil and water). To do this, the system 20 uses the multi-channel filter-photometer 30 (discussed below with reference to FIGS. 4A-4C) in conjunction with a process 100 of operation (discussed below with reference to FIG. 5).

Figure 4A:
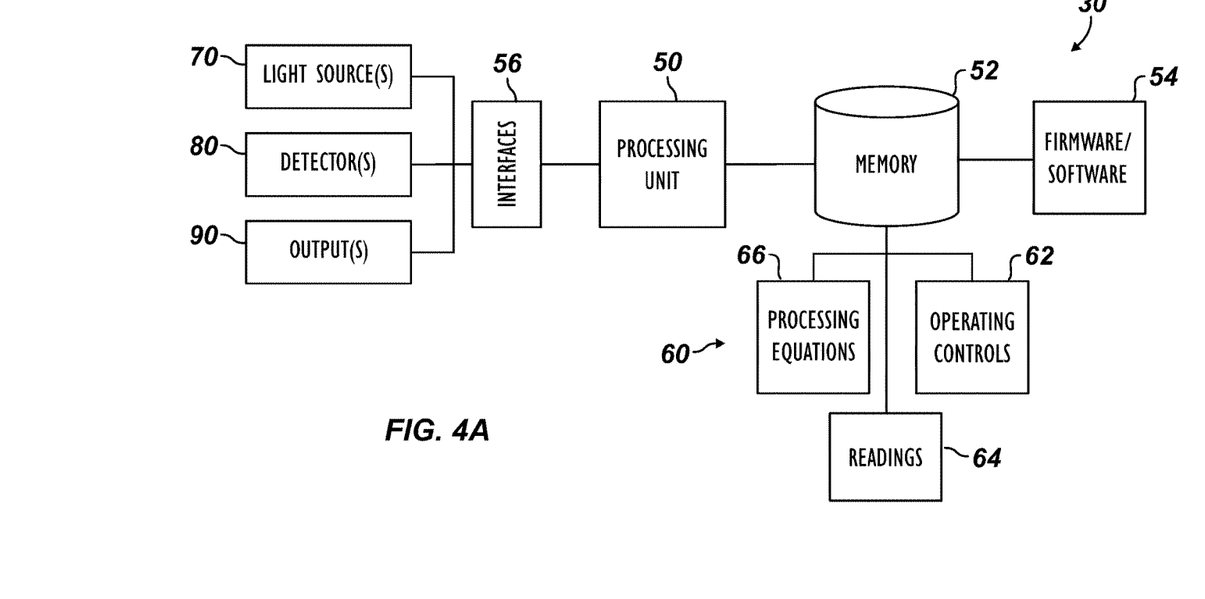
FIG. 4A illustrates a schematic view of a NIR water-cut meter for the disclosed system.
Figure 4B:
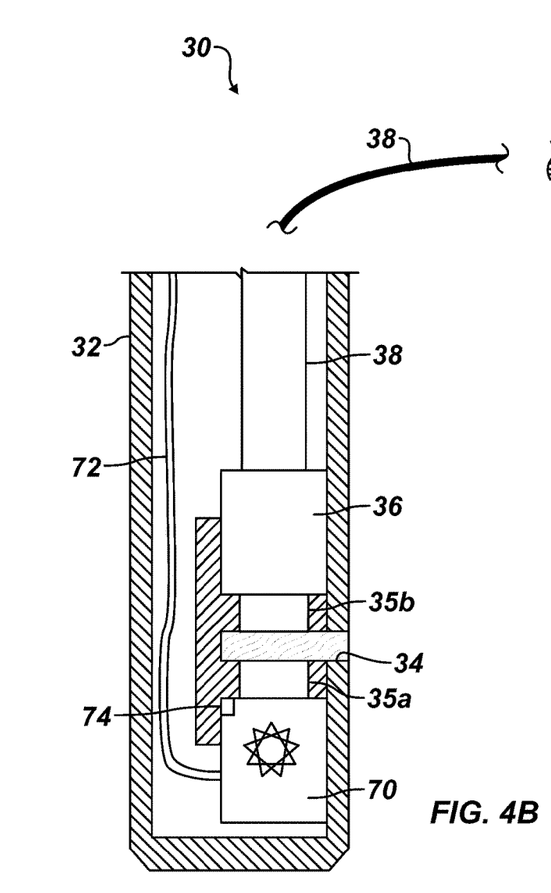
FIGS. 4B-4C illustrate components of the NIR water-cut meter for the disclosed system.

FIG. 4A illustrates a schematic view of a multi-channel filter-photometer 30 for the disclosed system (20). As noted, the photometer 30 can operate in the NIR spectral region. However, other spectral ranges could be used depending on the fluid components or other facets of the application. The elements of the photometer 30 shown in FIG. 4A can be incorporated into the probe (32), electronics package (31), and processing equipment (40) discussed above.

The photometer 30 includes a processing unit 50 operably connected to memory 52 and interfaces 56. The processing unit 50, memory 52, and interfaces 56 can be incorporated into one or both of electronics package (31) and processing equipment (40). The processing unit 50 can include any suitable processors and the like, and the memory 52 can include firmware and/or software 54 for operating the photometer 30.

The interfaces 56 connect with light source(s) 70, detector(s) 80, and output(s) 90. In general, the light source(s) 70 are associated with the probe (32) of the photometer 30, and the detector(s) 80 are associated with components in the probe (32) and the electronics package (31). The output(s) 90 can be associated with one or both of the electronics package (31) and the processing equipment (40) and can be displays, signals, etc. The interfaces 56 to the detectors 80 can include amplifiers, analog-to-digital converters, and other signal processing electronics.

For operation, the processing unit 50 accesses various operations/algorithms 60 stored in memory 52. The operations/algorithms 60 include operating controls 62, measurement operations 64, and processing equations 66, which may be part of the firmware/software 54. The operating controls 62 govern the overall operation of the photometer 30, such as illuminating the light source(s) 70, measuring with the detector(s) 80, outputting information, etc.

The measurement operations 64 store the measurement data and other readings of the photometer 30 in an appropriate format for access and processing. Some of the measurements and readings can include percent water-cut, liquid path length, hydrate inhibitor concentration, and temperature measurements. The processing equations 66 implement the calculations as disclosed below.

Figure 4C:
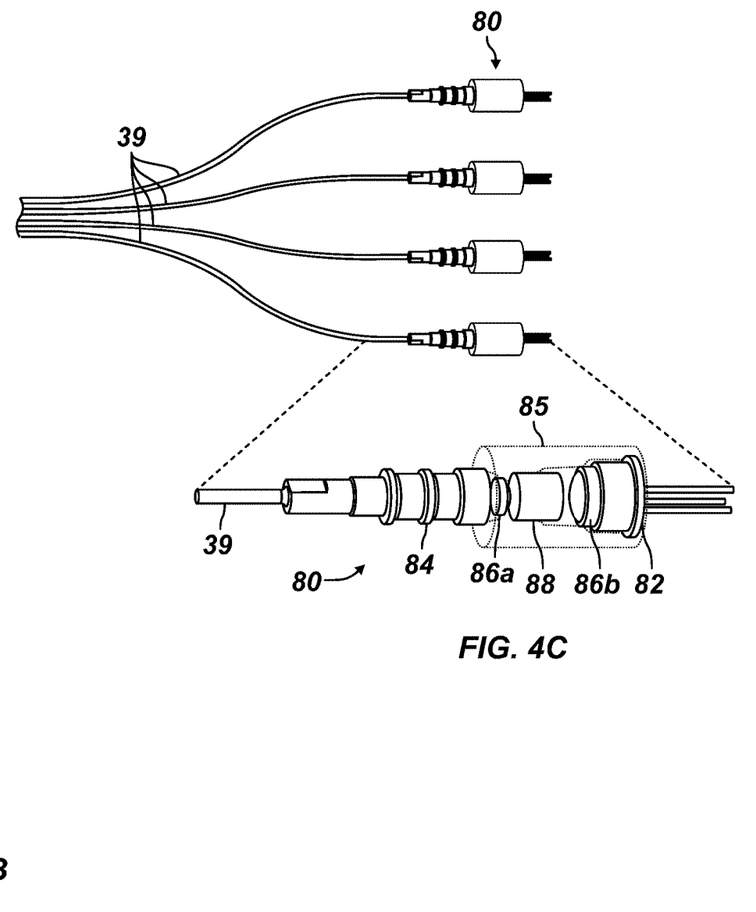

FIGS. 4B-4C illustrate some of the physical elements of the multi-channel filter-photometer 30 for the disclosed system (20). The probe 32 is shown in cross-section. The probe 32 houses the light source(s) 70 on one side of the measurement slot 34 and houses one or more optical elements 36, 38, etc. on another side of the measurement slot 34. Power/control signals from the electronics package (31) and the like connect through lines 72 in the probe 32 to the light source(s) 70. If necessary, one or more reference detectors 74 can be used to determine the transmitted intensity of the light source(s) 70, to monitor its operation, and the like. One or more detectors 74 can also measure reflectance of the transmitted energy from the multiphase flow so the reflectance can be used for various purposes.

A first window 35*a*, such as a sapphire window, allows the spectral energy from the light source(s) 70 to transmit through the measurement slot 34 and any mixture of fluid therein, and a second opposing window 35*b*, such as another sapphire window, allows the transmitted spectral energy to be collected by the one or more optical elements, which include collector optics 36 in optical communication with the second window 35*b*. A light pipe or a bundle 38 of fiber optical cables direct the transmitted spectral energy from the collector optics 36 to one or more detectors 80. The detector signals may be corrected for temperature of the detectors(s) 80 provided by a temperature sensing signal. Signal conditioning circuitry may be used and other available techniques may be applied.

The bundle 38 has numerous fibers, such as 10,000 fibers. They are grouped randomly into four grouped cables 39 (of about 2,500 fibers each) to deliver the spectral energy separately to four channels of the detectors 80. The random grouping of the fibers is meant to ensure that each of the detectors 80 receives transmitted spectral energy from a representative area of the window 35*b*. The number of fibers and the number of channels can be increased to improve analysis.

Each of the grouped cables 39 connect by optical couplings to the detectors 80. A representative optical coupling 84 is shown in FIG. 4C to connect a grouped cable 39 to a photodiode 82 of one of the detectors 80. To image the fibers of the grouped cable 39 onto the photodiode 82, a collimating lens 86*a* and a focusing lens 86*b* can be positioned in a lens housing 85 and can be separated by a lens spacer or spectral filter 88. The housing 85 having the lenses 86*a-b* and filter 88 attaches to the photodiode 82, which has a header and a window. On the other end, a fiber-ferrule assembly 84, strain relief boot, ferrule mounting tube, alignment sleeve, and the like, couple the grouped cable 39 to the housing 85. It will be appreciated that, rather than this optical coupling 84, other fiber and non-fiber-based arrangements could be used to image the spectral signals onto the photodiodes 82.

The filter photometer 30 measures absorbances at a number (usually 4 or 5) of discrete wavelengths, which in the present example are near-infrared. For example, the wavelengths can include 1110-nm, 1450-nm, 1632-nm, 1730-nm, and 1950-nm. The NIR emitter of the light source(s) 70 exposes the fluid mixture to broadband NIR radiation. The optical elements 36, 38, 39 collect and carry the transmitted spectral signal to the four channels of the detectors 80. The wavelengths are chosen for each channel based on distinct absorptive characteristics of expected components in the mixture. The relationship between component concentrations and measured absorbances is then exploited to calculate the component concentrations.

Analysis according to the present arrangement can be summarized as follows. The system is defined using absorbance equations (one for each wavelength) that contain several unknowns. The number of wavelengths are equal to or greater than the number of unknowns so that the system of equations can be solved. The main unknowns are water pathlength and oil pathlength (from which the water concentration can be calculated). The unknowns may additionally include 'scatter' and one or more non-homogeneity parameters.

Figure 5:
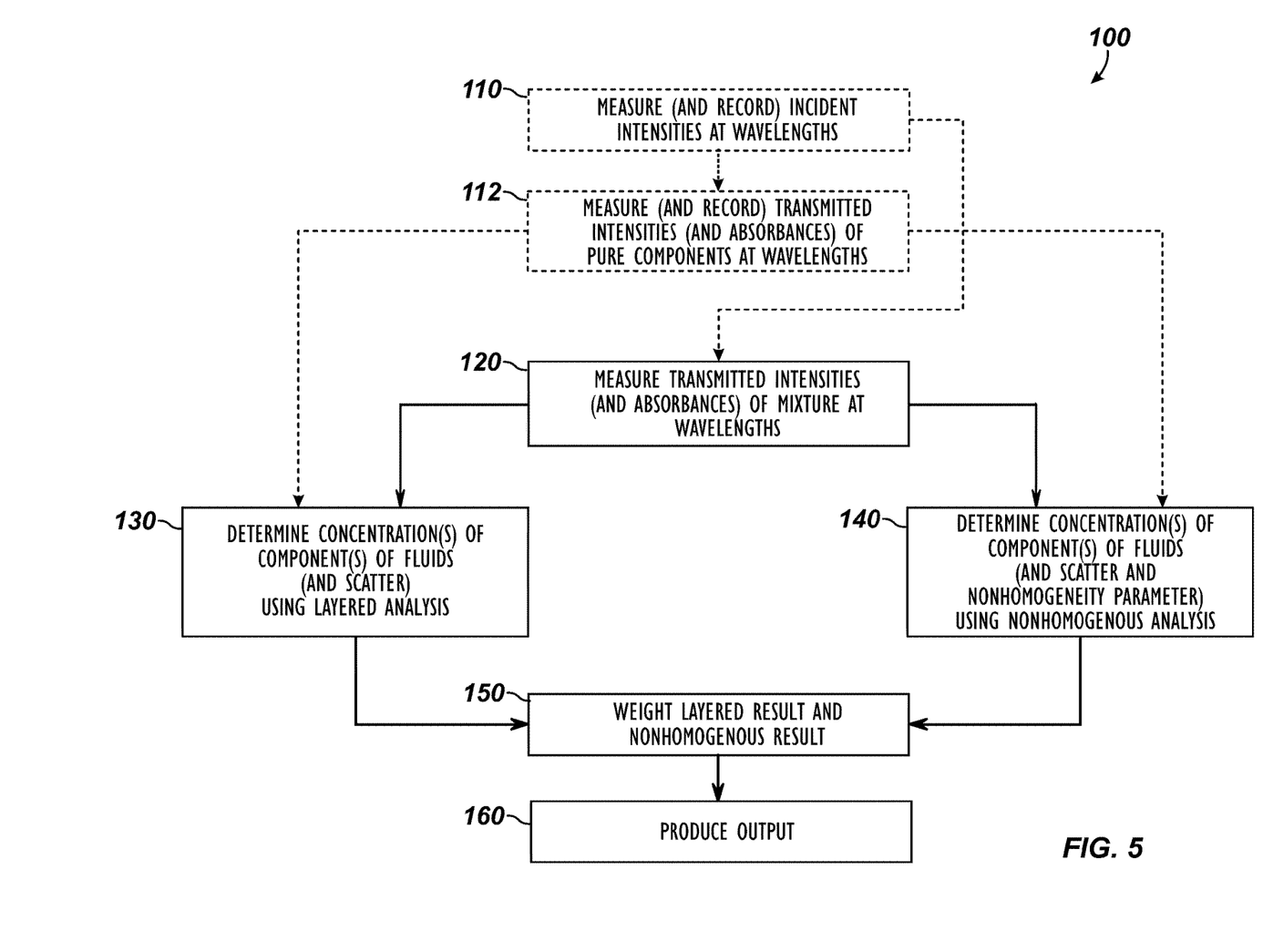
FIG. 5 illustrates a process of operation for the disclosed system.

FIG. 5 illustrates a process 100 of operation for the disclosed system (20) in performing the analysis summarized above. In one arrangement, the process 100 uses a nonhomogeneous analysis of the present disclosure alone to characterize the fluid mixture, which is represented by Block 140 of FIG. 5. In another arrangement and as expressly shown in FIG. 5, the process 100 uses the nonhomogeneous analysis of the present disclosure (Block 140) in combination with a layered analysis (from the prior art), which is represented by Block 130 of FIG. 5. Selection of a result from one form of analysis over another, weighting of one result over the other, or some other operation can be performed on the results from the two forms of analysis (Block 150) so final output can be provided (Block 160).

For both analyses (Block 130, 140), the photometer 30 measures (and records) the spectral intensities emitted at the wavelengths of interest (Block 110); this is a baseline calibration in air that represents the incident light $I_0$. The photometer 30 then measures (and records) the transmitted intensities I for pure components (such as 100% oil and 100% water) in the sensor slot 34 at the wavelengths of interest (Block 112); these are baseline pure-fluid calibrations (i.e., absorption coefficients, e.g., of oil and water). The absorption coefficients (Block 112) are known parameters in the system of equations for both analyses (Blocks 130, 140).

The baseline air calibration in Block 110 can be preconfigured as described above and/or adjusted in in real time using reference detectors 74.

With the calibrations done, the photometer 30 is then used to measure a mixture of interest during operation at an installation. With the probe 32 in the flow F and the mixture in the windowed slot 34, the photometer 30 measures the transmitted spectral intensities (and absorbances) of the mixture at the wavelengths of interest (Block 120); this is the primary 'raw' measurement. Analysis using the baseline measurements and the primary raw measurement can then follow one or both forms of analyses (Blocks 130, 140).

The layered analysis (Block 130) is based on the Beer-Lambert law adapted for an immiscible homogeneous condition (as described above with reference to FIG. 1B). In general, the layered analysis (Block 130) can incorporate techniques known and used in the art, such as those disclosed in the incorporated patents, to determine concentration(s) of the component(s) in the fluid (Block 130).

At the same time of the layered analysis (Block 130) or separately as the case may be, the process 100 performs the nonhomogeneous analysis (Block 140) according to the present disclosure. The nonhomogeneous analysis (Block 140) assumes the existence of a plurality of cells or columns in the fluid layer (as noted above with respect to FIG. 3A) to account for a nonhomogeneous distribution of the components in the mixture. The analysis solves the disclosed system of equations (described below) to determine concentration(s) of the component(s) in the mixture and to determine non-homogeneity of the mixture.

Similar to the layered analysis (Block 130), the nonhomogeneous analysis (Block 140) disclosed here also uses the Beer-Lambert law, but it uses a mathematical correction for nonhomogeneity. When this nonhomogeneity correction is applied to the absorbances measured by the NIR filter photometer 30, component concentration measurements are emphatically more accurate.

The absorbance equations for the nonhomogeneous analysis (Block 140) are determined as follows. Knowing the initial intensity $I_0$ of the incident spectral energy from the baseline measurement (or some other reference measurement), knowing the absorption of water $a_w$ at the specified wavelength, knowing the absorption of oil $a_o$ at the specified wavelength, and defining the total number N of cells, the measured absorbance can be written as:

$$\text{Abs}_{meas} = \ln\left(\frac{\sum_{j=1}^{N}\left(\frac{I_o}{N}\left(e^{a_w b_{w,j}+a_o b_{o,j}+Sc_j}\right)\right)}{I_o}\right) = \ln\left(\text{mean}\left[e^{a_w b_{w,j}+a_o b_{o,j}+Sc_j}\right]\right) \quad (\text{eq. 1})$$

where: $I_0$=incident spectral intensity,
N=total number of cells,
$a_w$=wavelength-specific water absorption,
$a_o$=wavelength-specific oil absorption,
$b_{w,j}$=optical path length of water in cell j,
$b_{o,j}$=optical path length of oil in cell j,
$Sc_j$=scatter in cell j, and
j=cell number.

From this equation of the measured absorbance, the goal is to determine the unknowns, namely, average path length $b_w$ (mean[$b_{w,j}$]) of water, average path length $b_o$ (mean[$b_{o,j}$]) of oil, average scatter (mean[$Sc_j$]), and one or more non-homogeneity parameters that come out of the system of equations.

For the sake of illustration, the special case of a Gaussian distribution of $b_w$ and $b_o$ in the N fluid columns is assumed (not shown). Furthermore, the liquid pathlength is assumed to be equal (say, 1, as shown in FIG. 3C) for all cells. Neither of these assumptions affect the general validity of the disclosed methodology.

With these assumptions, the above equation for the measured absorbance can be rewritten as:

$$\text{Abs}_{meas} = a_w \cdot \text{mean}\,[b_{w,j}] + a_o \cdot \text{mean}\,[b_{o,j}] + \text{mean}[Sc_j] + \frac{\left(\begin{array}{c}a_w^2 \cdot \text{var}[b_{w,j}] + a_o^2 \cdot \text{var}[b_{o,j}] + \\ \text{var}[Sc_j] + 2 \cdot a_w \cdot a_o \cdot \text{Cov}[b_{w,j}, b_{o,j}]\end{array}\right)}{2}$$

which further reduces to $$\text{Abs}_{meas} = a_w \cdot \text{mean}\,[b_{w,j}] + a_o \cdot \text{mean}\,[b_{o,j}] +$$

$$\left(\text{mean}[Sc_j] + \frac{\text{var}[Sc_j]}{2}\right) + (a_w^2 - a_o^2) \cdot \frac{\text{var}[b_{w,j}]}{2}$$

which can then be written simply as $$\text{Abs}_{meas} = a_w \cdot b_w + a_o \cdot b_o + Sc' + (a_w^2 - a_o^2) \cdot WF \quad \text{(eq. 2)}$$

where the "Waviness Factor" WF is representative of the non-homogeneity of the fluid mixture.

As noted earlier, the WF parameter is analogous to the slope of the division between the water and oil paths in the cells in FIG. 3A. Overall, the presence of the WF parameter in the model (or system of equations) allows for a better, more accurate solution for the concentrations of the nonhomogeneous mixture. The WF parameter can also be used to describe the non-homogeneity of the mixture, can be used as a diagnostic parameter, and can indicate a need for changing flow rates or making other changes in the measurements.

Equation (2) above is derived assuming a Gaussian distribution of components (e.g., oil and water) in the sensor slot. Other distributions can be assumed to produce different forms for equation (2) as will be appreciated by one skilled in the art having the benefit of the present disclosure.

As will be recognized, the scatter parameter $S_c'$ accounts for the attenuation of the transmitted energy due to a number factors independent of the specific wavelengths used. Thus, the scatter parameter $S_c'$ is the same for each of the wavelengths, even though the value of scatter may change due to changes in flow/process conditions (e.g., sand content) or intensity of light source 70 (e.g., aging).

As equation (2) above shows, the absorbance measurement $\text{Abs}_{meas}$ is characterized as a first function of at least two optical pathlengths ($b_o$; $b_w$) of the at least two immiscible components (o-oil, w-water), a scatter parameter (i.e., wavelength-independent scatter factor Sc') of the mixture, and a non-homogeneity parameter (i.e., waviness factor WF) of the mixture. The wavelength-specific water and oil absorption values $a_w$ and $a_o$ are known. As noted above with respect to FIGS. 3A-3C, the non-homogeneity parameter (WF) uses a plurality of cells (i) of the transmitted spectral energy through the mixture in which the at least two pathlengths ($b_{o,i}$; $b_{w,i}$) of the at least two immiscible components (o-oil, w-water) are different for each cell (i).

Because equation (2) has four unknown variables—i.e., the pathlengths $b_w$ and $b_o$ for the water and oil, the scatter factor (Sc'), and the waviness factor (WF), at least four absorbance measurements $\text{Abs}_{meas}$ must be made (at four wavelengths) so that the system of equations can be solved. The unknown variables are then determined by solving the system of equations using standard techniques (such as least squares minimization). In the end, the path lengths $b_w$ and $b_o$ for the water and oil are determined, and the concentrations of the components in the fluid mixture are determined using the determined path lengths.

It is worth noting that the nonhomogeneous equations (2), at least for the special case of a Gaussian distribution of path lengths, reduce seamlessly to the simpler layered equations (given above with reference to FIG. 1B) when appropriate assumptions are applied.

As noted earlier, the above set of equations (2) have been derived for the special case of a Gaussian distribution (of oil and water path lengths). Other distributions will yield a different systems of absorbance equations. In general, the disclosed methodology is valid regardless of the assumed distribution.

The layered analysis (FIG. 5 Block 130) requires the measured absorbances from at least three wavelengths to solve for the unknown variables. The nonhomogeneous analysis (FIG. 5 Block 140), with the assumption of Gaussian distribution, requires measured absorbances from at least four wavelengths to solve for the unknown variables. For other (non-Gaussian) distributions, more wavelengths may be needed, but the general methodology remains the same.

In the process 100, the layered analysis (Block 130) and the nonhomogeneous analysis (Block 140) can then be used independently or together for the final output. Depending on the concentration of water in the mixture compared to oil, for example, the layered analysis (Block 130) may be more or less applicable than the nonhomogeneous analysis (Block 140). For instance, the layered analysis (Block 130) tends to be better suited for analysis when there is lower water content in the mixture. However, the nonhomogeneous analysis (Block 140) tends to be better suited for analysis when there is a higher water content in the mixture (when the mixture is typically more nonhomogeneous). To that end, the process 100 can determine the final output from a balance, a selection, a weighting, or the like of the two forms of analysis (Blocks 130, 140).

As shown in the present example, the process 100 can use a weighted average at Block 150 between concentrations determined through the layered analysis (Block 130) and the nonhomogeneous analysis (Block 140) and produce the desired output from the weighting (Block 160). The weighting can be scaled appropriately, such as in a linear fashion. Other forms of combining the two results can be used based on the water content of the mixture (or other measured parameters) to improve accuracy.

Figure 6A:
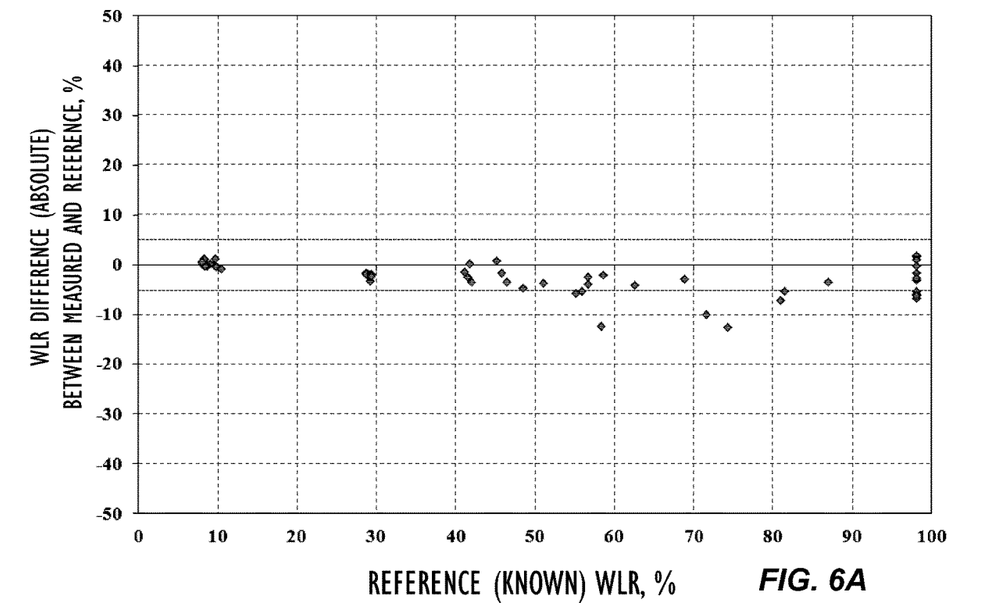
FIGS. 6A-6B graph comparative results for the disclosed system and prior art.
Figure 6B:
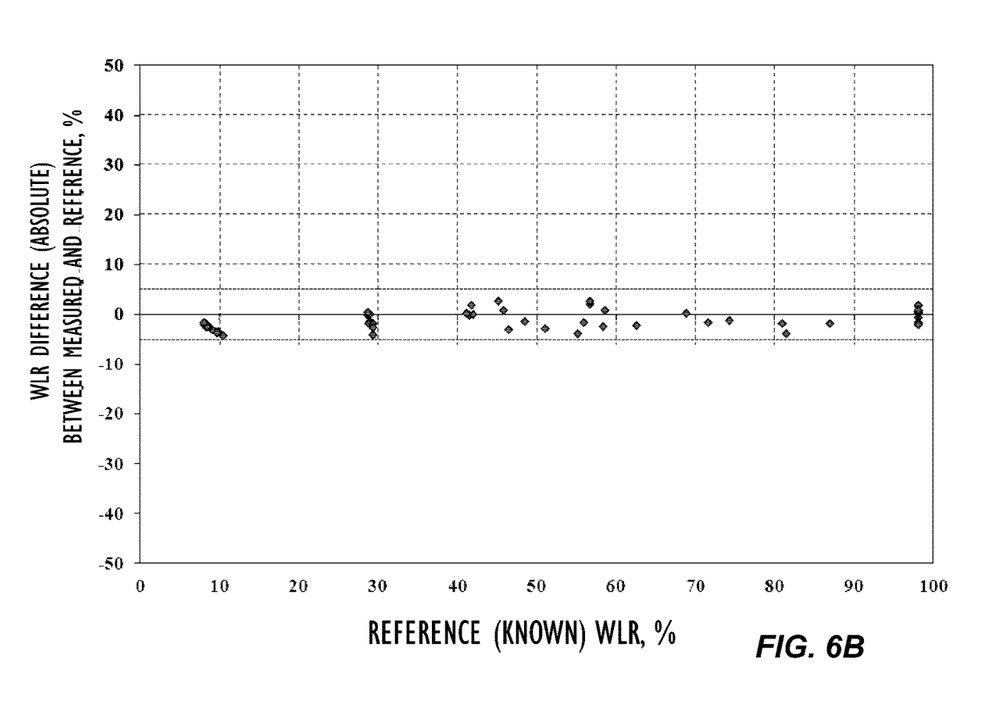

To illustrate how the layered analysis (Block 130) and nonhomogeneous analysis (Block 140) differ, FIGS. 6A-6B graph the difference (in absolute terms) between measured and reference Water Liquid Ratio WLR ($\Delta$WLR %) for the two forms of analysis with data obtained from a multiphase flow loop for a wide range of WLR and gas volume fractions. FIG. 6A illustrates results of the layered analysis (Block 130) and FIG. 6B illustrates results of the nonhomogeneous analysis (Block 140) for the same set of testpoints. For the lower end of the water liquid ratio (WLR %), the layered analysis (Block 130) shown in FIG. 6A tends to be more accurate. However, for the higher end of the water liquid ratio (WLR %), the nonhomogeneous analysis (Block 140) shown in FIG. 6B tends to be more accurate. This weighting based on the water liquid ratio can be step-wise, linear, or the like.

The process 100 of FIG. 5 can be integrated into the near-infrared (NIR) filter photometer 30 so the disclosed techniques can measure component concentrations in multiphase flows in the field.

For continuous monitoring by the photometer (30), the process 100 of FIG. 5 then repeats over time, and the photometer (30) records the readings. The system (20) monitors the readings and performs appropriate actions, such as generating alarms, notifying other well systems, etc.

Detected values of reference (backside) detector(s) 74 can be added to the absorbance equation if necessary to account for changes in NIR source 70 output with aging. In this way, rather than using initial baseline measurements of the initial intensity stored for later reference, the initial intensity of the emitted spectral energy can be detected with one or more current reference measurements, and the detected initial intensity from the one or more reference measurements can be used directly in the determination of the absorbance measurements disclosed herein.

The measurements in Blocks 130, 140 based on NIR absorption photometry are not limited to oil and water; they can further take advantage of the unique absorption profiles of water, oil, natural gas, methanol, glycol, etc., and can use the overtone absorption bands for O—H and C—H bonds. Additional wavelength bands can be measured simultaneously to enable additional component differentiations (e.g., oil, water, gas, glycol, and methanol). Wavelength bands are measured for particular applications, and calculations determine relative concentrations of individual components.

A flowmeter (e.g., flowmeter 26 schematically depicted in FIG. 2) can measure the flow stream, and liquid volume flow can be calculated. An amount of water can then be calculated by multiplying the liquid volume by the calculated water cut, WC. An amount of liquid hydrocarbon is also calculated by multiplying the liquid volume by (100-WC %). The calculated amount of liquid hydrocarbon and the calculated amount of water may be totaled over time.

Although the methods described here are in the context of NIR filter photometry, the concepts are not dependent on the spectral/wavelength range—it can be extended to other spectral ranges, such as UV/Vis and Gamma.

In the teachings of the present disclosure, the processing unit 50 can include any one or more suitable processing elements, application-specific integrated circuits, chips, field programmable arrays, etc. and can include any one or more suitable memory or storage elements 52. As will be appreciated, for example, teachings of the present disclosure can be implemented in digital electronic circuitry, computer hardware, computer firmware, computer software, or any combination thereof. Teachings of the present disclosure can be implemented in a programmable storage device (computer program product tangibly embodied in a machine-readable storage device) for execution by a programmable control device or processor so that the programmable processor executing program instructions can perform functions of the present disclosure. The teachings of the present disclosure can be implemented advantageously in one or more computer programs that are executable on a programmable system including at least one programmable processor coupled to receive data and instructions from, and to transmit data and instructions to, a data storage system, at least one input device, and at least one output device. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A method of measuring a mixture in a multiphase flow, the mixture being nonhomogeneous and having at least two immiscible components, the method comprising:
   emitting spectral energy of at least four wavelengths at initial intensity for transmission through the mixture;
   detecting transmitted spectral energy of the at least four wavelengths at resultant intensity after transmission through the mixture;
   determining, from the initial and resultant intensities, an absorbance measurement of the mixture at each of the at least four wavelengths;
   characterizing each of the absorbance measurements as a first function of: at least two pathlengths of the at least two immiscible components, a scatter parameter, and a non-homogeneity parameter, the scatter parameter representing attenuation of the transmitted spectral energy independent of the wavelengths, the non-homogeneity parameter representing non-homogeneity of the mixture using a plurality of cells of the transmitted spectral energy through the mixture in which the at least two pathlengths of the at least two immiscible components are different for each cell; and
   determining, from the characterization of the absorbance measurements as the first function, first concentrations of the at least two immiscible components in the mixture.

2. The method of claim 1, wherein determining, from the characterization of the absorbance measurements, the first concentrations of the at least two immiscible components in the mixture comprises:
   solving for the at least two pathlengths of the at least two immiscible components from the characterization of the absorbance measurements; and
   determining, from the solution of the at least two pathlengths, the first concentrations of the at least two immiscible components in the mixture.

3. The method of claim 1, wherein emitting the spectral energy comprises emitting near-infrared light.

4. The method of claim 1, wherein detecting the transmitted spectral energy of the at least four wavelengths at the resultant intensity after transmission through the mixture comprises detecting at the wavelengths of 1110-nm, 1450-nm, 1632-nm, 1730-nm, and 1950-nm.

5. The method of claim 1, further comprising:
   detecting the initial intensity of the emitted spectral energy with a reference measurement; and
   using the detected initial intensity from the reference measurement in the determination of the absorbance measurements.

6. The method of claim 1, further comprising initially calibrating the emission of the spectral energy at the initial intensity by obtaining a baseline measurement of the initial intensity transmitted without the mixture.

7. The method of claim 6, comprising storing the baseline measurement and using the stored baseline measurement for the initial intensity in the determination of the absorbance measurements.

8. The method of claim 1, further comprising initially calibrating the detection of the transmitted spectral energy by detecting the transmitted spectral energy at a first of the resultant intensity after transmission through only a first of the at least two immiscible components of the mixture and detecting the transmitted spectral energy at a second of the resultant intensity after transmission through only a second of the at least two immiscible components of the mixture.

9. The method of claim 8, further comprising deriving absorption coefficients for the first and second immiscible components of the mixture by analyzing the first and second resultant intensities.

10. The method of claim 1, wherein characterizing each of the absorbance measurements as the first function comprises using the Beer-Lambert law at each of the cells.

11. The method of claim 10, wherein the non-homogeneity parameter representing the non-homogeneity of the components in the mixture comprises a value analogous to a slope for a division in the cells between a first of the at least two pathlengths for water, as one of the at least two immiscible components, and a second of the at least two pathlengths for oil, as another of the at least two immiscible components.

12. The method of claim 11, wherein determining, from the characterization of the absorbance measurements as the first function, the first concentrations of the at least two immiscible components in the mixture comprises solving for unknown variables of the water path length, the oil path length, the scatter parameter, and the non-homogeneity parameter from the four functions for the absorbances measurements at four of the at least four wavelengths.

13. The method of claim 1, wherein detecting the transmitted spectral energy of the wavelengths at the resultant intensity after transmission through the mixture comprises transmitting the transmitted spectral energy in a plurality of sets of randomized bundles of optical fibers respectively to a plurality of photodiodes.

14. The method of claim 1, further comprising:
characterizing each of at least three of the absorbance measurements as a second function based on the mixture having homogeneous layers of the at least two immiscible components; and
determining, from the characterization of the absorbance measurements as the second function, second concentrations of the at least two immiscible components in the mixture.

15. The method of claim 14, further comprising:
selecting the first and second concentrations; and
determining a final output for final concentrations of the components based on the selection.

16. The method of claim 15, wherein selecting the first and second concentrations comprises weighting the first and second concentrations based on a ratio of water, as one of the at least two immiscible components, relative to total liquid volume in the mixture.

17. The method of claim 16, wherein weighting comprises favoring the first concentrations for a higher ratio of the water relative to the total liquid volume in the mixture, and favoring the second concentrations for a lower ratio of the water relative to the total liquid volume in the mixture.

18. The method of claim 1, further comprising:
measuring the multiphase flow through piping;
calculating a liquid volume of the measured flow; and
calculating a ratio of water, as one of the at least two immiscible components, relative to the liquid volume by multiplying the calculated liquid volume by the first concentration determined for water.

19. A non-transitory program storage device comprising instructions stored thereon to cause an apparatus for analyzing a nonhomogeneous mixture of immiscible components in a multiphase flow to:
emit spectral energy of at least four wavelengths at initial intensity for transmission through the mixture;
detect transmitted spectral energy of the at least four wavelengths at resultant intensity after transmission through the mixture;
determine, from the initial and resultant intensities, an absorbance measurement of the mixture at each of the at least four wavelengths;
characterize each of the absorbance measurements as a function of at least two pathlengths of the at least two immiscible components, a scatter parameter, and a non-homogeneity parameter, the scatter parameter representing attenuation of the transmitted spectral energy independent of the wavelengths, the non-homogeneity parameter representing the non-homogeneity of the mixture using a plurality of cells of the transmitted spectral energy through the mixture in which the at least two pathlengths of the at least two immiscible components are different for each cell; and
determine, from the characterization of the absorbance measurements as the function, concentrations of the at least two immiscible components in the mixture.

20. An apparatus for analyzing a nonhomogeneous mixture of immiscible components in a multiphase flow, the apparatus comprising:
a probe having first and second windows, the first and second windows opposing one another by a gap for the fluid in the flow;
one or more sources emitting spectral energy of at least four wavelengths at initial intensity from the first window for transmission through the mixture in the gap to the second window;
one or more detectors in optical communication with the second window and detecting transmitted spectral energy of the at least four wavelengths at resultant intensity after transmission through the fluid; and
a processing unit in communication with the one or more detectors and configured to:
determine, from the initial and resultant intensities, an absorbance measurement of the mixture at each of the at least four wavelengths;
characterize each of the absorbance measurements as a function of at least two pathlengths of the at least two immiscible components, a scatter parameter, and a non-homogeneity parameter, the scatter parameter representing attenuation of the transmitted spectral energy independent of the wavelengths, the non-homogeneity parameter representing the non-homogeneity of the mixture using a plurality of cells of the transmitted spectral energy through the mixture in which the at least two pathlengths of the at least two immiscible components are different for each cell; and
determine, from the characterization of the absorbance measurements as the function, concentrations of the at least two immiscible components in the mixture.

* * * * *